(12) United States Patent
Sgroi, Jr.

(10) Patent No.: US 11,192,227 B2
(45) Date of Patent: Dec. 7, 2021

(54) RELOAD ASSEMBLY FOR CIRCULAR STAPLING DEVICES

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/878,094

(22) Filed: May 19, 2020

(65) Prior Publication Data
US 2021/0016426 A1    Jan. 21, 2021

Related U.S. Application Data

(60) Provisional application No. 62/874,534, filed on Jul. 16, 2019.

(51) Int. Cl.
| A61B 17/00 | (2006.01) |
| B25C 5/16 | (2006.01) |
| B25C 5/15 | (2006.01) |
| A61B 17/29 | (2006.01) |

(52) U.S. Cl.
CPC ............ B25C 5/162 (2013.01); B25C 5/1686 (2013.01); *A61B 2017/2946* (2013.01); *B25C 5/15* (2013.01)

(58) Field of Classification Search
CPC ...... A61B 17/07207; A61B 2017/2946; A61B 17/1155
USPC .......... 227/175.1, 175.2, 175.4, 176.1, 182.1
See application file for complete search history.

(56) References Cited

U.S. PATENT DOCUMENTS

| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| CA | 908529 A | 8/1972 |
| CA | 2805365 A1 | 8/2013 |

(Continued)

OTHER PUBLICATIONS

European Search Report dated Dec. 15, 2020, issued in corresponding EP Appln. No. 20185269, 7 pages.

*Primary Examiner* — Hemant Desai
*Assistant Examiner* — Jacob A Smith

(57) ABSTRACT

A reload assembly includes a shell housing, a knife carrier, a lockout component, and a hook component. The lockout component is supported on an inner wall of the knife carrier and has a body formed of a resilient material that defines a window. The hook component is supported on the inner housing portion of the shell housing and includes a body having a hook that is received within the window of the lockout component when the knife carrier is in its retracted position after the reload assembly has been fired to obstruct readvancement of the knife carrier.

14 Claims, 15 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |

(56) References Cited

U.S. PATENT DOCUMENTS

| | | | |
|---|---|---|---|
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,694,865 B2 * | 4/2010 | Scirica ................. A61B 17/072 227/175.2 |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |

(56) References Cited

U.S. PATENT DOCUMENTS

| | | |
|---|---|---|
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,589 B2 * | 12/2012 | Boudreaux ...... A61B 17/07207 227/175.4 |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 * | 10/2013 | Nalagatla ............. H04B 7/0673 227/175.1 |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,044 B2 * | 12/2013 | Hueil ...................... A61B 50/30 227/175.2 |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |

(56) References Cited

U.S. PATENT DOCUMENTS

| | | |
|---|---|---|
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1* | 1/2014 | Williams ............ A61B 17/1155 227/179.1 |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0085120 A1* | 3/2018 | Viola ............... A61B 17/00491 |

FOREIGN PATENT DOCUMENTS

| | | |
|---|---|---|
| DE | 1057729 B | 5/1959 |
| DE | 8301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2730238 A1 | 5/2014 |
| EP | 3701886 A1 | 9/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

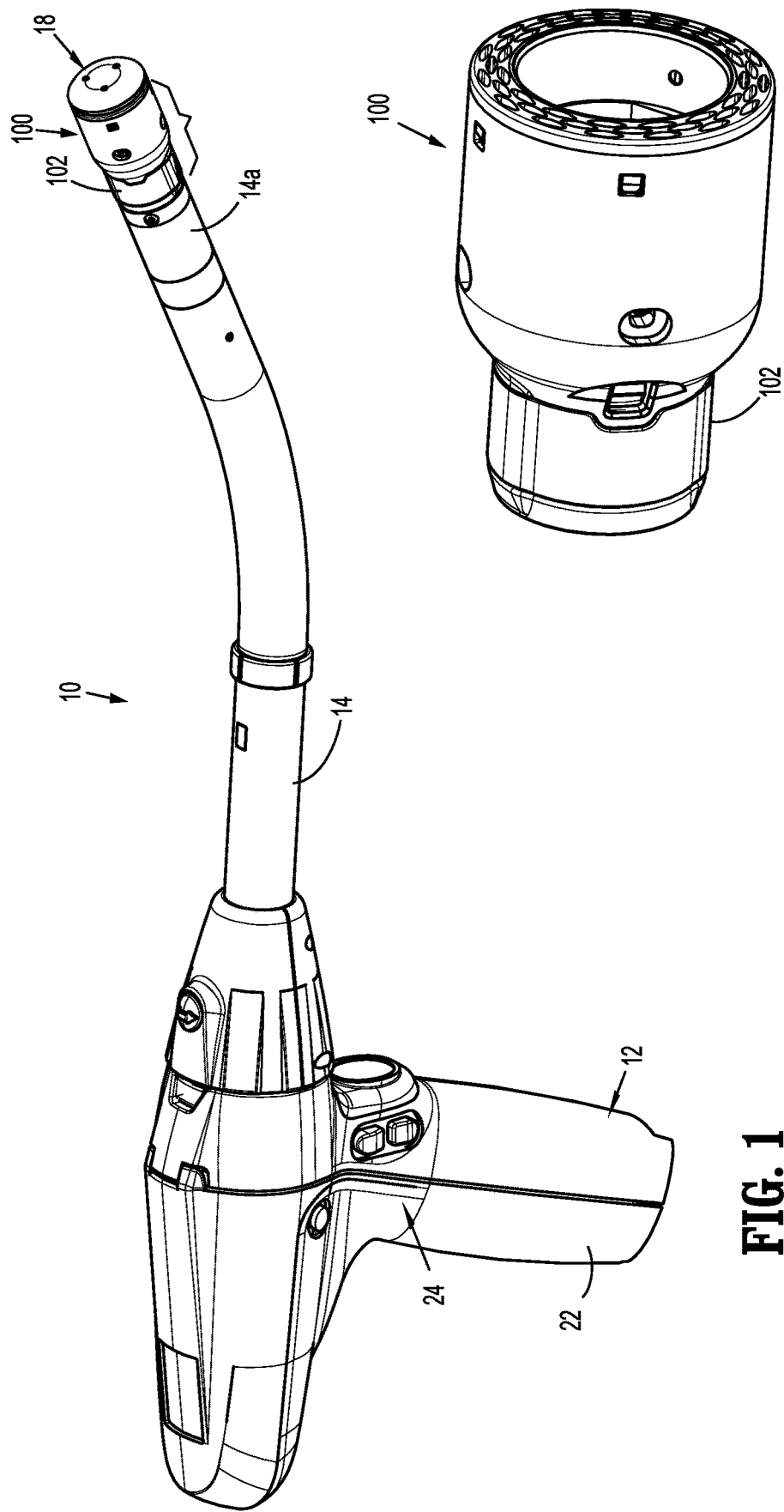

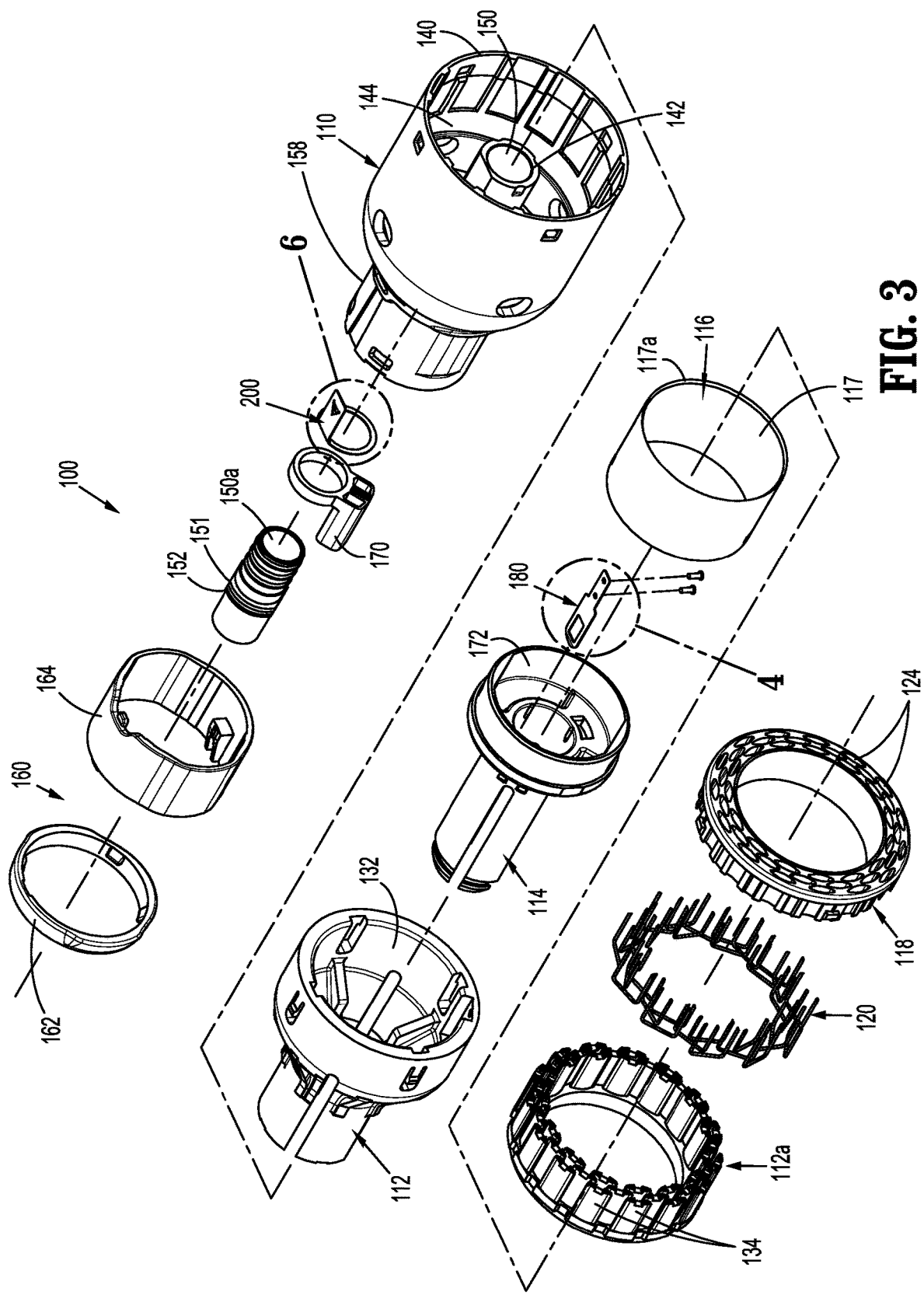

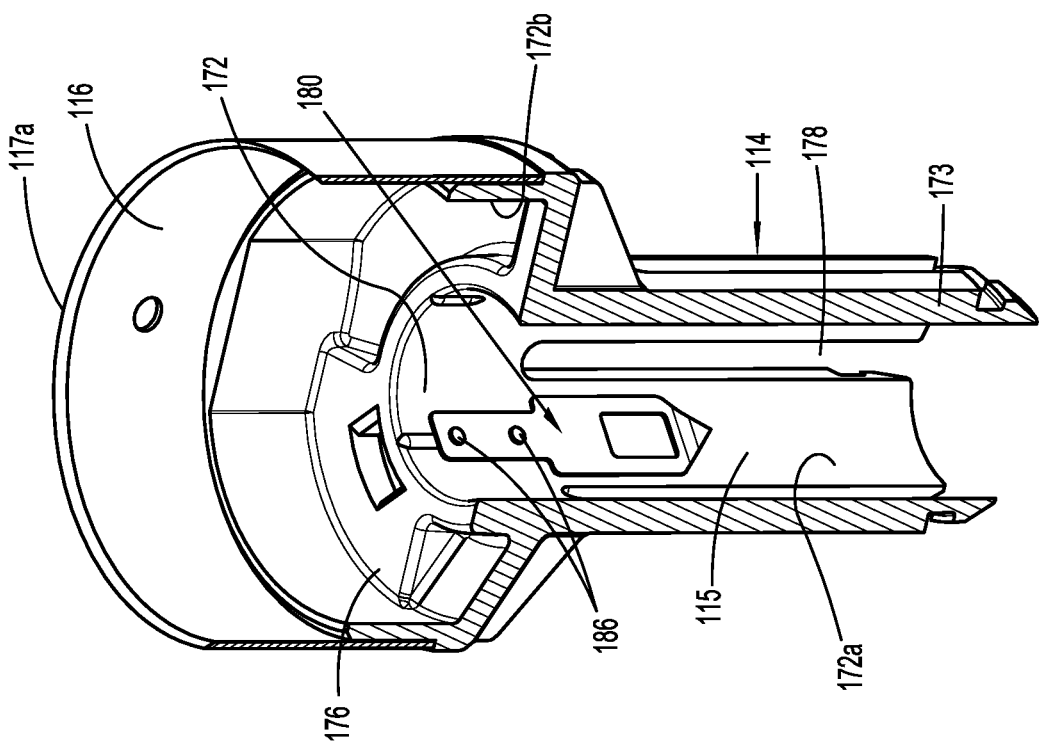
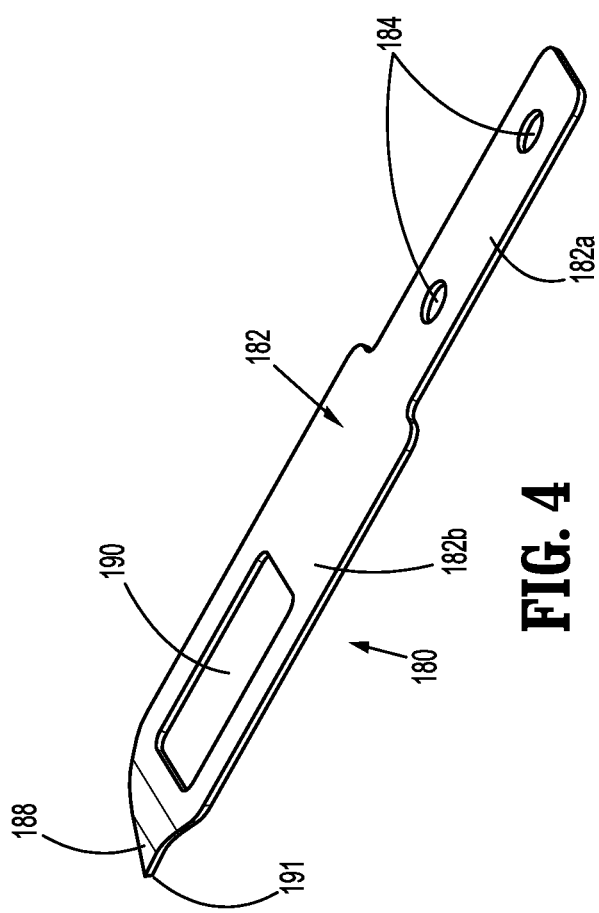

RELOAD ASSEMBLY FOR CIRCULAR STAPLING DEVICES

CROSS-REFERENCE TO RELATED APPLICATIONS

This application claims the benefit of and priority to U.S. Provisional Patent Application Ser. No. 62/874,534 filed Jul. 16, 2019, the entire disclosure of which is incorporated by reference herein.

BACKGROUND

1. Technical Field

The present disclosure is directed to circular stapling devices and, more particularly, to reload assemblies for circular stapling devices with structure to retain a knife carrier in a retracted position after the stapling device is fired.

2. Background of Related Art

Conventional circular stapling devices include an elongate body and a shell or reload assembly that is supported on a distal portion of the elongate body. The reload assembly includes a shell housing, a staple cartridge supported on the shell housing having a plurality of staples, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core or cut tissue After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife to such a degree that removal of the tissue donut from within the cavity defined by the knife is difficult. A continuing need exists in the art for a reload assembly that includes improved structure for retaining the knife/knife carrier in a retracted position.

SUMMARY

One aspect of the disclosure is directed to a reload assembly including a shell housing, a staple cartridge, a pusher, a knife carrier, a lockout component, and a hook component. The shell housing includes an inner housing portion and an outer housing portion that is spaced from the inner housing portion to define an annular cavity between the inner and outer housing portions. The staple cartridge is supported on a distal portion of the shell housing and defines a plurality of staple pockets that receive staples. The pusher is supported within the annular cavity of the shell housing and is movable between a retracted position and an advanced position to eject the staples from the staple cartridge. The knife carrier includes a body that defines a longitudinal axis and supports a knife. The body of the knife carrier includes an inner wall defining a central bore. The inner housing portion of the shell housing is positioned within the central bore of the knife carrier such that the knife carrier is movable about the inner housing portion of the shell housing between advanced and retracted positions. The lockout component is supported on the inner wall of the knife carrier, has a body formed of a resilient material, and defines a window. The hook component is supported on the inner housing portion of the shell housing and includes a body having a hook that is received within the window of the lockout component when the knife carrier is in its retracted position after the reload assembly has been fired to obstruct readvancement of the knife carrier.

Another aspect of the disclosure is directed to a circular stapling device including an elongate body having a proximal portion and a distal portion and a reload assembly. The reload assembly includes a shell housing, a staple cartridge, a pusher, a knife carrier, a lockout component, and a hook component. The shell housing includes an inner housing portion and an outer housing portion that is spaced from the inner housing portion to define an annular cavity between the inner and outer housing portions. The staple cartridge is supported on a distal portion of the shell housing and defines a plurality of staple pockets that receive staples. The pusher is supported within the annular cavity of the shell housing and is movable between a retracted position and an advanced position to eject the staples from the staple cartridge. The knife carrier includes a body that defines a longitudinal axis and supports a knife. The body of the knife carrier includes an inner wall defining a central bore. The inner housing portion of the shell housing is positioned within the central bore of the knife carrier such that the knife carrier is movable about the inner housing portion of the shell housing between advanced and retracted positions. The lockout component is supported on the inner wall of the knife carrier, has a body formed of a resilient material, and defines a window. The hook component is supported on the inner housing portion of the shell housing and includes a body having a hook that is received within the window of the lockout component when the knife carrier is in its retracted position after the reload assembly has been fired to obstruct readvancement of the knife carrier.

In embodiments, the lockout component includes a resilient body that has a lockout member positioned proximally of the window, wherein the resilient body is positioned between the hook component and the knife carrier when the knife carrier is in a retracted position prior to firing of the reload assembly.

In some embodiments, the hook is angled downwardly towards the inner housing portion of the shell housing.

In certain embodiments, the hook component includes a proximal mounting portion that is secured to the inner housing portion such that the hook component is supported in cantilevered fashion to the inner housing portion of the shell housing.

In embodiments, the lockout component is positioned to pass between the hook component and the inner housing portion of the shell housing when the knife carrier is returned from its advanced position to its retracted position after the reload assembly has been fired to position the hook of the hook component within the window of the lockout component.

In some embodiments, the lockout component includes a distal mounting portion that is secured to the inner wall of the knife carrier to secure the lockout component to the knife carrier in cantilevered fashion.

In certain embodiments, the hook of the hook component has a proximal portion connected to the body and a tip that engages the inner housing portion of the shell assembly, wherein the tip is positioned proximally of the proximal portion of the hook.

Another aspect of the disclosure is directed to a reload assembly including a shell housing, a staple cartridge, a knife carrier, a first locking component, and a second locking component. The shell housing includes an inner housing portion, an outer housing portion, and at least one guide portion positioned between the inner and outer housing portions. The inner housing portion is spaced from the outer housing portion to define an annular cavity between the inner and outer housing portions. The staple cartridge is supported on a distal portion of the shell housing and defines a plurality of staple pockets that receive staples. The knife carrier includes a body defining a longitudinal axis and supporting a knife. The body of the knife carrier includes a plurality of longitudinally extending body portions that are spaced from each other to define longitudinal slots that receive the at least one guide portion of the shell housing. The longitudinally extending portions include inner walls that define a central bore. The inner housing portion of the shell housing is positioned within the central bore of the knife carrier such that the knife carrier is movable about the inner housing portion of the shell housing between advanced and retracted positions. The first locking component is supported on the at least one guide portion of the shell housing and includes a resilient body having a first hook that extends radially outward of the at least one guide portion. The second locking component is supported on the inner wall of the knife carrier and includes a body formed from a resilient material having a second hook that extends radially inward into the central bore of the knife carrier. When the knife carrier is in a pre-fired retracted position, the second locking component is positioned between the first locking component and the at least one guide portion of the shell housing such that the first and second hooks are misaligned, and when the knife carrier is in a post-fired retracted position, the second hook component is positioned radially outward of the first hook component such that the first and second hooks are aligned to obstruct readvancement of the knife carrier.

In embodiments, the first and second locking components are formed of leaf springs.

In some embodiments, the first hook of the first locking component includes a distal portion having a distally facing tapered surface and the second hook of the second locking component includes a proximal portion having a proximally facing tapered surface, wherein the distally facing tapered surface engages the proximally facing tapered surface as the knife carrier is moved from its advanced position to its retracted position to allow the second locking component to pass over the first locking component.

BRIEF DESCRIPTION OF THE DRAWINGS

Various embodiments of the disclosed reload assembly are described herein below with reference to the drawings, wherein:

FIG. 1 is a side perspective view of a circular stapling device including an exemplary embodiment of the disclosed reload assembly in accordance with the present disclosure;

FIG. 2 is a side perspective view of the reload assembly of FIG. 1;

FIG. 3 is an exploded side perspective view of the reload assembly of FIG. 2;

FIG. 4 is an enlarged view of the indicated area of detail shown in FIG. 3;

FIG. 5 is a cross-sectional view of a knife carrier of the reload assembly shown in FIG. 3;

DETAILED DESCRIPTION OF EMBODIMENTS

Figure 7:
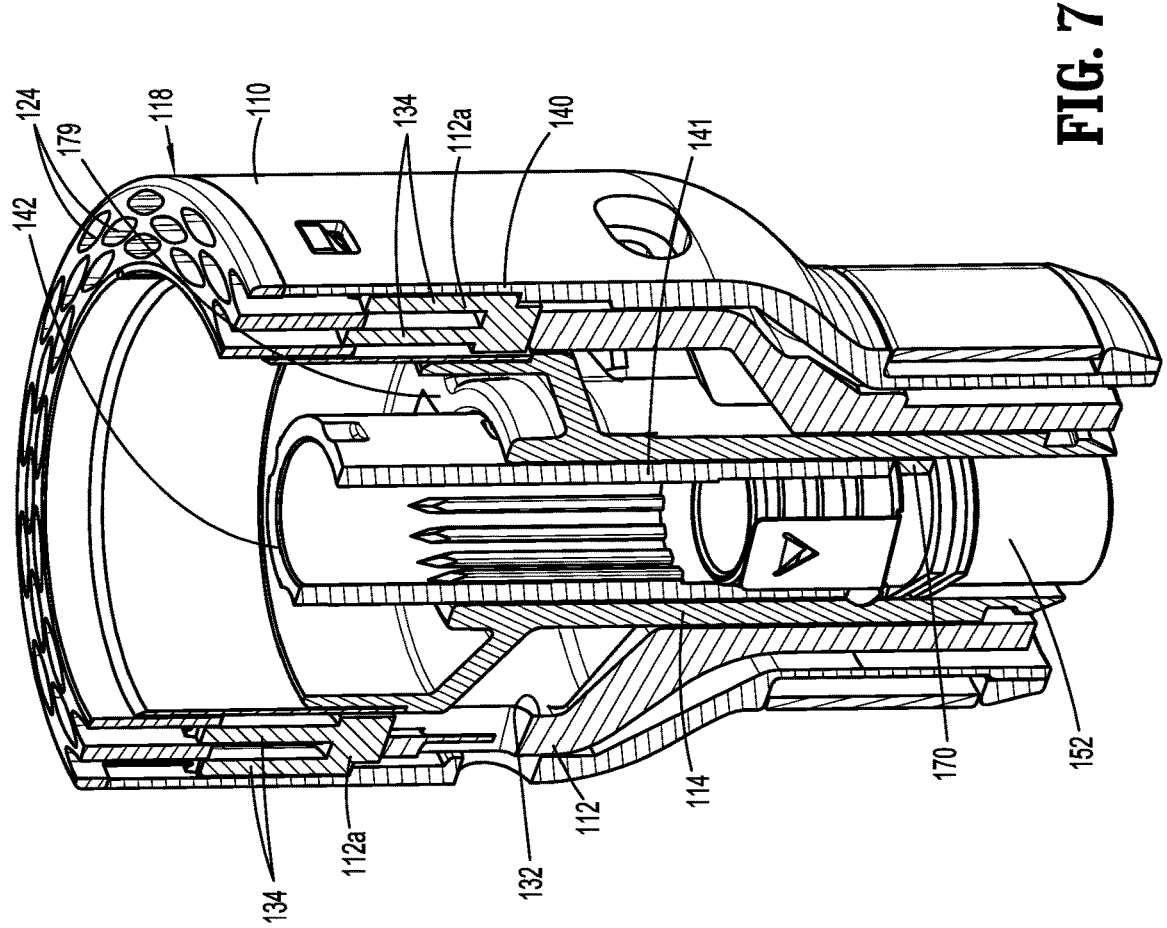
FIG. 7 is a perspective, cross-sectional view of the reload assembly shown in FIG. 3 taken through the longitudinal axis of the reload assembly with the reload assembly in a pre-fired condition.

The disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In addition, directional terms such as front, rear, upper, lower, top, bottom, distal, proximal, and similar terms are used to assist in understanding the description and are not intended to limit the present disclosure.

In this description, the term "proximal" is used generally to refer to that portion of the device that is closer to a clinician, while the term "distal" is used generally to refer to that portion of the device that is farther from the clinician. In addition, the term "endoscopic" is generally used to refer to endoscopic, laparoscopic, arthroscopic, and/or any other procedure conducted through small diameter incision or cannula. Further, the term "clinician" is used generally to refer to medical personnel including doctors, nurses, and support personnel.

FIGS. 1 and 2 illustrate a circular stapling device 10 including an exemplary embodiment of the disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. The reload assembly 100 includes a proximal portion 102 that is releasably coupled to a distal portion 14a of the elongate body 14. The handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. No. 9,055,943 (the '943 Patent), U.S. Pat. No. 9,023,014 (the '014 Patent), and U.S. Publication Nos. 2018/0125495, and 2017/0340351 which are incorporated herein by reference in their entirety. Alternately, it is envisioned that the present disclosure could also be incorporated into a manually powered stapling device such as disclosed in U.S. Pat. No. 7,303,106 (the '106 Patent) or a stapling device that is configured for use with a robotic system such as disclosed in U.S. Pat. No. 9,962,159 (the '159 Patent) that does not include a handle assembly. The '106 and '159 Patents are also incorporated herein by reference in their entirety.

Referring to FIGS. 2 and 3, the reload assembly 100 includes a shell housing 110, a staple actuator 112, a staple pushing member 112a, a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one of the plurality of staples 120. The staple actuator 112 and the staple pushing member 112a together define a longitudinal through-bore 132. The staple actuator 112 has a distal portion that abuts a proximal portion of the staple pushing member 112a such that distal movement of the staple actuator 112 within the shell housing 110 causes distal movement of the staple pushing member 112a. The staple pushing member 112a of the reload 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 130 is moved from a retracted position to an advanced position within the shell housing 110.

The shell housing 110 includes an outer housing portion 140 and an inner housing portion 142 that are spaced from each other to define an annular cavity 144 between the inner and outer housing portions 140 and 142. The staple actuator 112, the staple pushing member 112a, the knife carrier 114, and the annular knife 116 are movable within the annular cavity 144 of the shell housing 110 between retracted and advanced positions. The staple actuator 112 and the staple pushing member 112a are movable from their retracted positions to their advanced positions independently of the knife carrier 114 and annular knife 116 to eject the staples 120 from the staple cartridge 118. The annular knife 116 defines a cylindrical cavity 117, is supported about an outer surface of the knife carrier 114 and includes a distal cutting edge 117a. The knife carrier 114 and annular knife 116 are movable within the through-bore 132 of the staple actuator 112. After the staple actuator 112 and staple pushing member 112a are moved from their retracted positions to their advanced positions, the knife carrier 114 can be moved from its retracted position to its advanced position to cut tissue positioned radially inward of the staple cartridge 118.

The inner housing portion 142 of the shell housing 110 defines a through-bore 150 (FIG. 3) that receives an anvil shaft (not shown) of the anvil assembly 18. For a more detailed description of an exemplary anvil assembly 18, see, e.g., the '106 Patent. The through-bore 150 has a proximal portion that receives a bushing 152 that defines a through-bore 150a that is coaxial and forms an extension of the through-bore 150 of the inner housing portion 142. In embodiments, the bushing 152 is formed of a high strength material, e.g., metal, to provide added strength to the inner housing portion 142 of the shell housing 110 and includes an annular flange 151.

The shell housing 110 includes a proximal portion 158 (FIG. 3) that supports a coupling mechanism 160 (FIG. 2) that is operable to releasably couple the reload assembly 100 to the adaptor assembly 14 of the stapling device 10 (FIG. 1) to facilitate replacement of the reload assembly 100 and reuse of the stapling device 10. The coupling mechanism 160 includes a retaining member 162 and a coupling member 164. The coupling member 164 is received about the proximal portion 158 (FIG. 3) of the shell housing 110 and is configured to engage the distal portion 14a (FIG. 1) of the adaptor assembly 14 to couple the reload assembly 100 to the adaptor assembly 14. It is envisioned that other coupling mechanisms can be used to secure the reload assembly 100 to the adaptor assembly 14.

The reload assembly 100 may include an e-prom holder 170 (FIG. 3) that is supported on the shell housing 110 and is configured to support an e-prom (not shown). As is known in the art, an e-prom can communicate with the adaptor assembly 14 to provide information to the adaptor assembly 14 and the handle assembly 12 related to characteristics of the reload assembly 10.

Referring to FIGS. 3-5, the knife carrier 114 is movably positioned within the through-bore 132 (FIG. 6) of the staple actuator 112 and staple pushing member 112a between its retracted and advanced positions and defines a stepped central bore 172. The stepped central bore 172 includes a small diameter proximal portion 172a (FIG. 5) and a larger diameter distal portion 172b. The proximal portion 172a of the central bore 172 of the knife carrier 114 receives the inner housing portion 142 (FIG. 8) of the shell housing 110 such that the knife carrier 114 slides about the inner housing portion 142.

The knife carrier 114 defines an annular shoulder 176 (FIG. 5) that is positioned between the proximal portion 172a and the distal portion 172b of the central bore 172. The proximal portion 172a of the central bore 172 is defined by longitudinally extending body portions 173 (FIG. 5) that are separated from each other by longitudinal slots 178. The longitudinal slots 178 receive guide portions 179 (FIG. 7) of the shell housing 110 to limit the knife carrier 114 to longitudinal movement within the annular cavity 144 of the shell housing 110 as the knife carrier 114 moves between its advanced and retracted positions. The proximal portion 172a of knife carrier 114 includes an inner wall surface 115 (FIG. 5) that supports a lockout component 180 (FIG. 4).

In embodiments, the lockout component 180 includes a resilient body 182 (FIG. 4) that has a distal mounting portion 182a and a proximal locking portion 182b. The distal mounting portion 182a of the resilient body 182 is secured to the inner wall 115 of the knife carrier 114 in cantilevered fashion. In embodiments, the distal mounting portion 182a defines two openings 184 that receive screws or rivets 186 (FIG. 5) to secure the distal mounting portion 182a of the lockout component 180 to the inner wall surface 115 of the knife carrier 114. Alternately, the lockout component 180 can be secured to the knife carrier 114 using a variety of known attachment techniques. The proximal locking portion 182b of the lockout component 180 includes a proximally positioned lockout member 188 and defines a window or opening 190 that is positioned between the lockout member 188 and the distal mounting portion 182a. In embodiments, the lockout member 188 is angled inwardly into the central bore 172 of the knife carrier 114 and defines an apex or tip 191.

Figure 6:
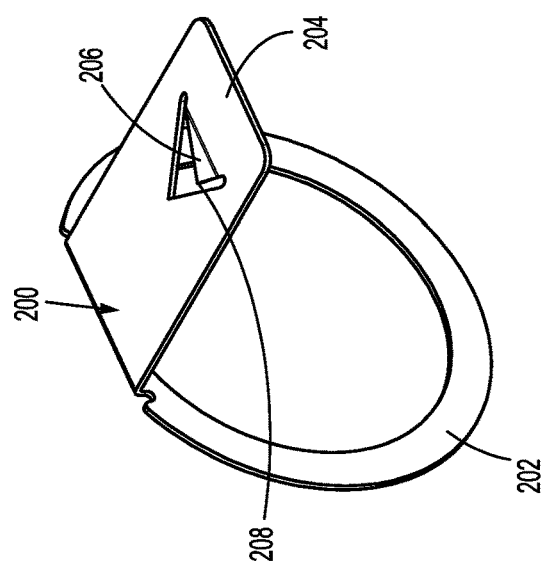
FIG. 6 is an enlarged view of the indicated area of detail shown in FIG. 3.
Figure 8:
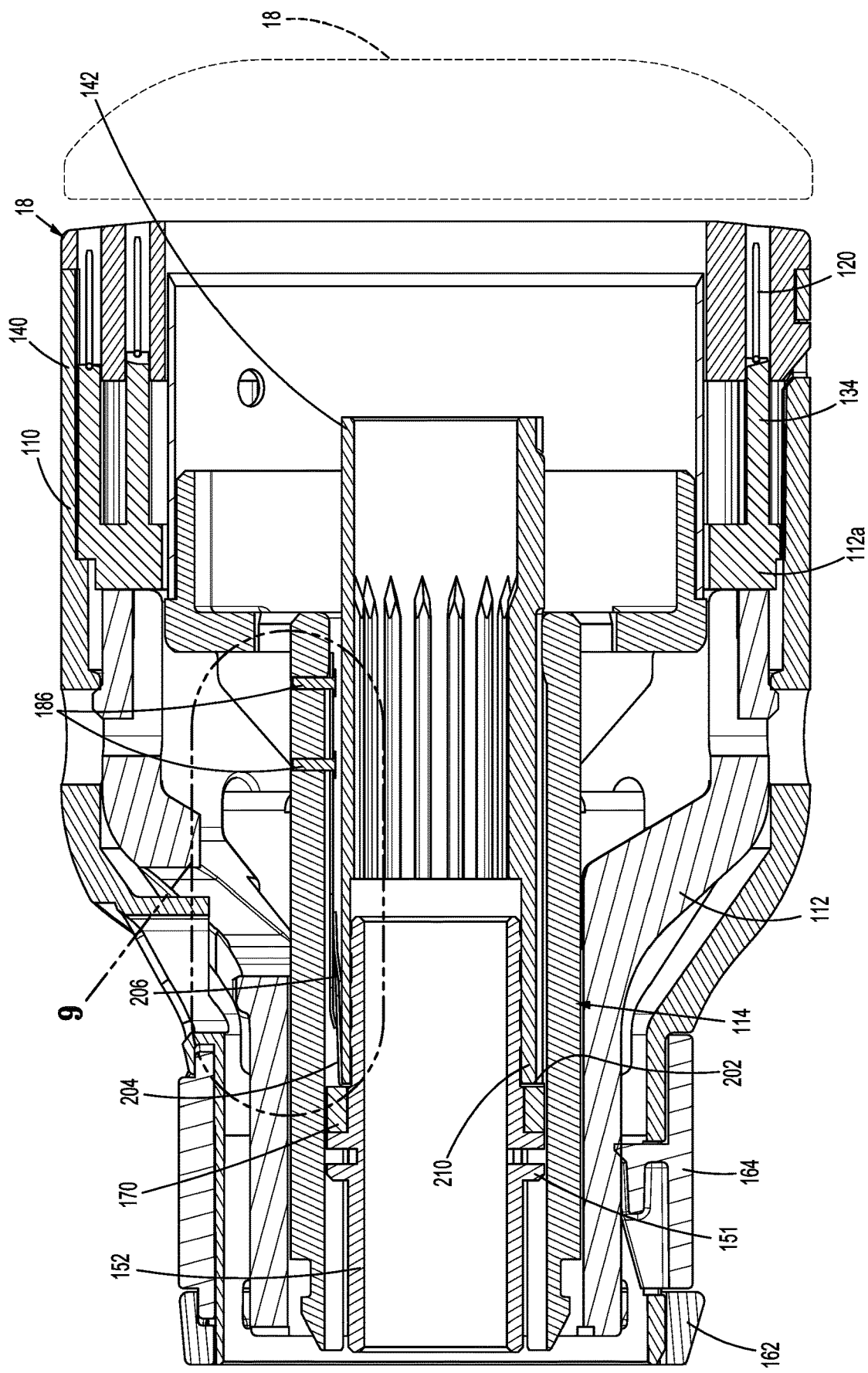
FIG. 8 is a cross-sectional view of the reload assembly shown in FIG. 3 taken through the longitudinal axis of the reload assembly with the reload assembly in a pre-fired condition.
Figure 9:
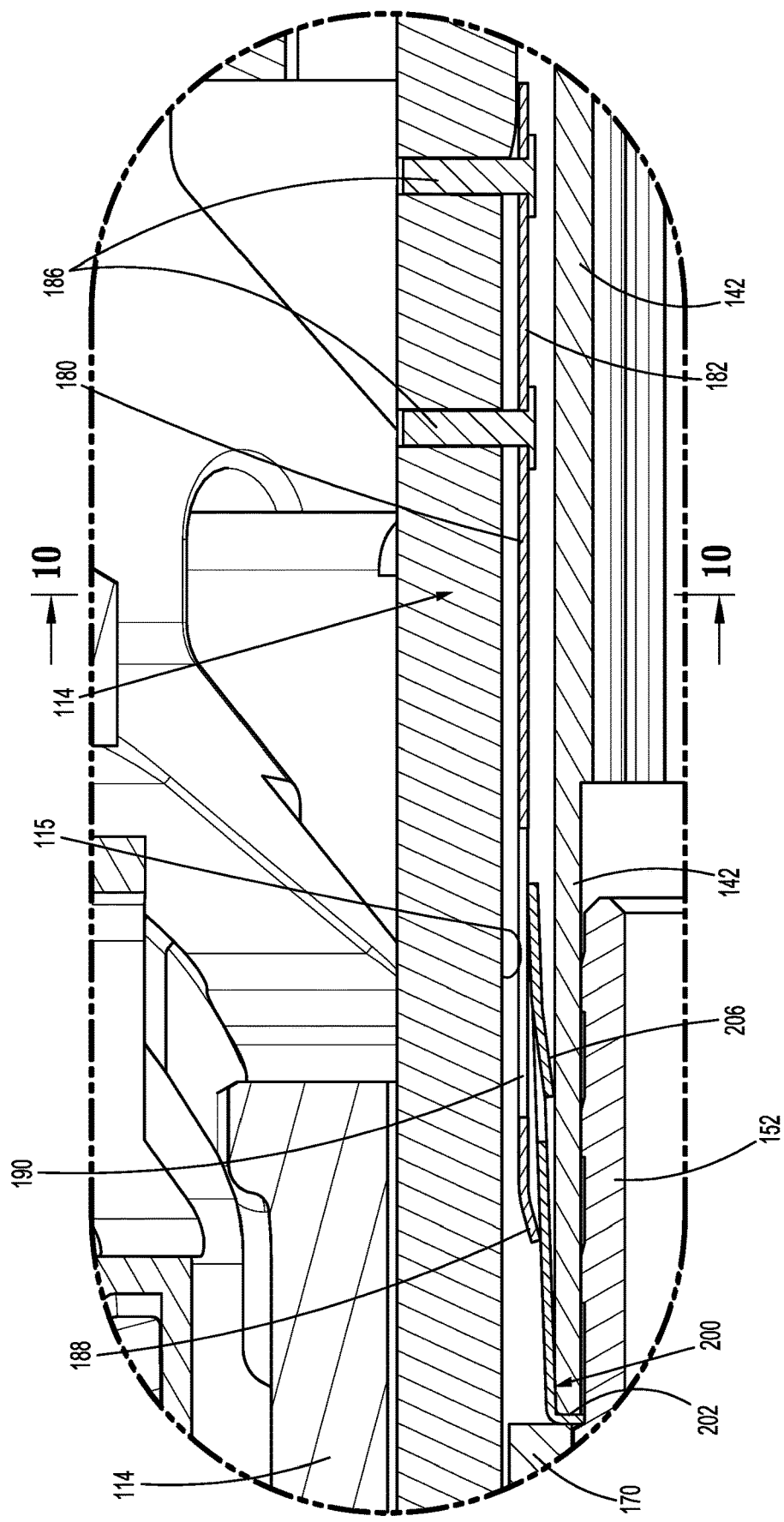
FIG. 9 is an enlarged view of the indicated area of detail shown in FIG. 8.
Figure 10:
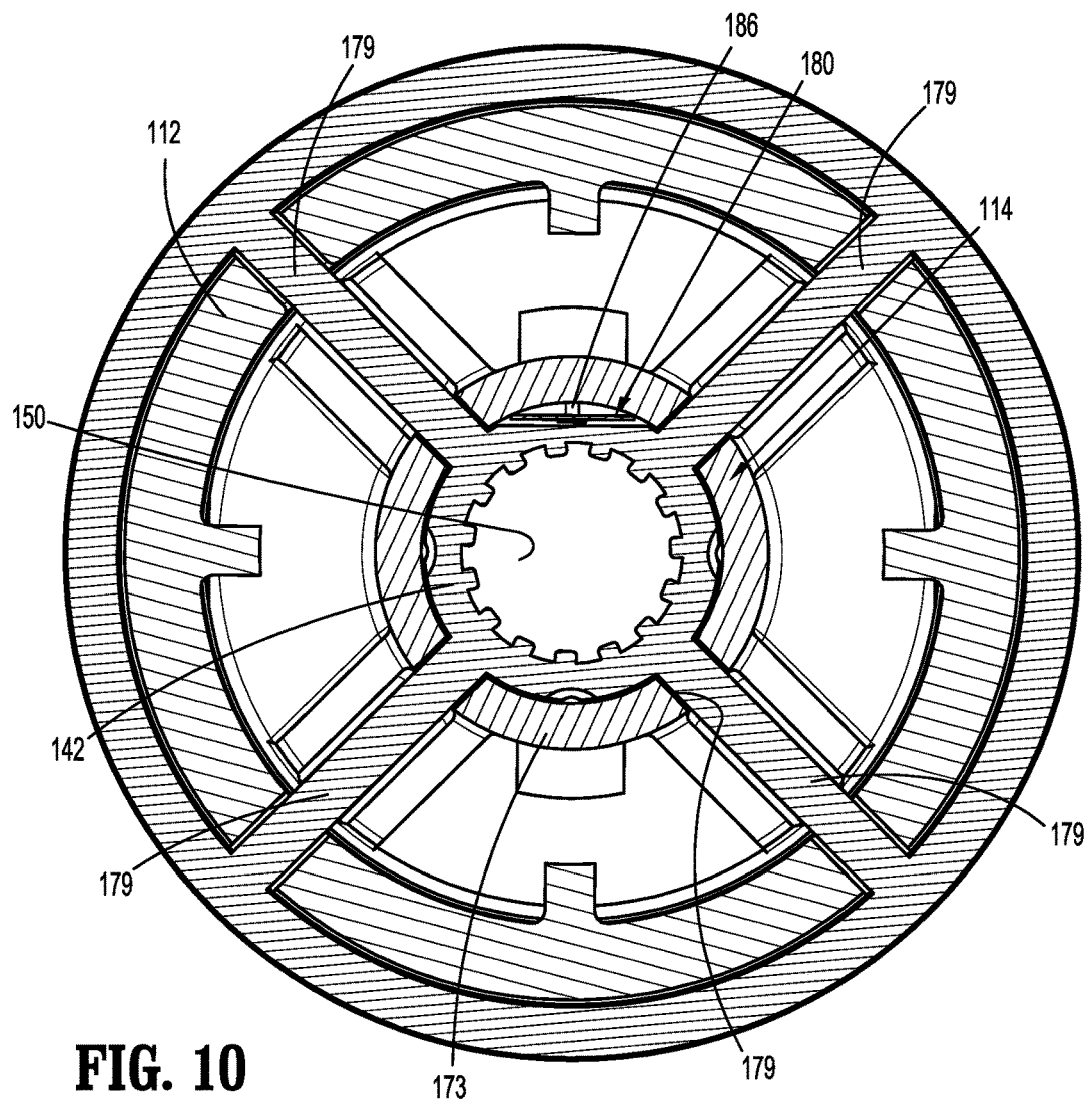
FIG. 10 is a cross-sectional view taken along section line 10-10 of FIG. 9.
Figure 11:
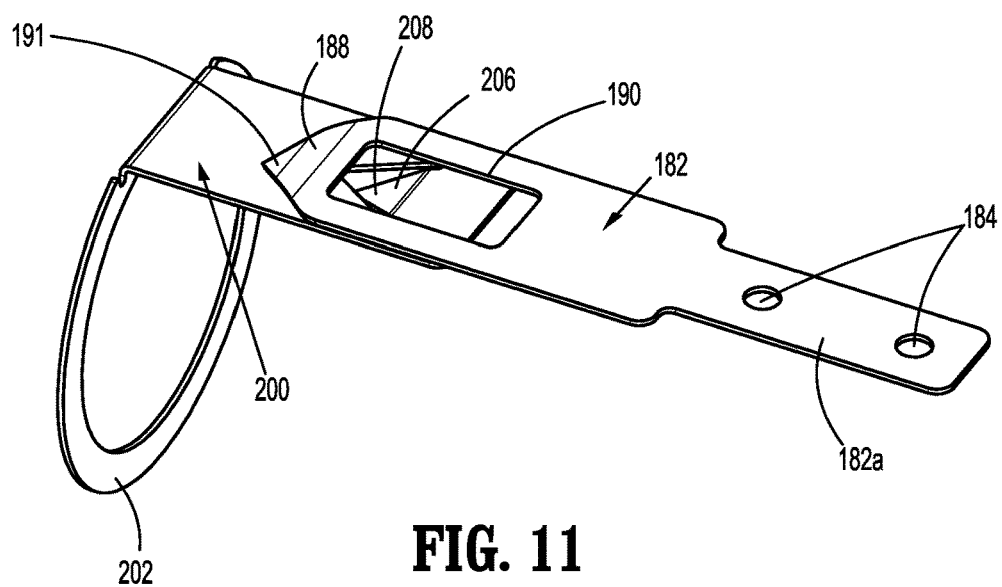
FIG. 11 is a side perspective view of a lockout component of the reload assembly shown in FIG. 3.

Referring to FIGS. 6-8, the inner housing portion 142 of the shell housing 110 supports a hook component 200 that includes a proximal mounting portion 202 and a body 204 including a hook 206 having a tip or apex 208. In embodiments, the mounting portion 202 is an annular member and is received about the bushing 152 between the flange 151 of the bushing 152 and the proximal end 210 of the inner housing portion 142 such that the body 204 including the hook 206 is positioned distally of the mounting portion 202 with the tip 208 of the hook 206 extending in a direction proximally from the body 204. In embodiments, the hook component 200 is supported by the mounting portion 202 in cantilevered fashion with the hook 206 biased into engagement with the inner housing portion 142 of the shell housing 110.

Referring to FIGS. 8-11, when the reload assembly 100 is assembled and the knife carrier 114 is in a retracted position within the shell housing 110, the lockout component 180, which is secured to the inner wall surface 115 of the knife carrier 114, is in a retracted position radially outward of and engaged with the hook component 200 such that the lockout component 180 is biased outwardly of the inner housing portion 142 of the shell housing 110. In this position, the hook 206 of the hook component 200 is positioned beneath the window 190 of the lockout component 180 and is engaged with the inner housing portion 142 of the shell housing 110.

Figure 12:
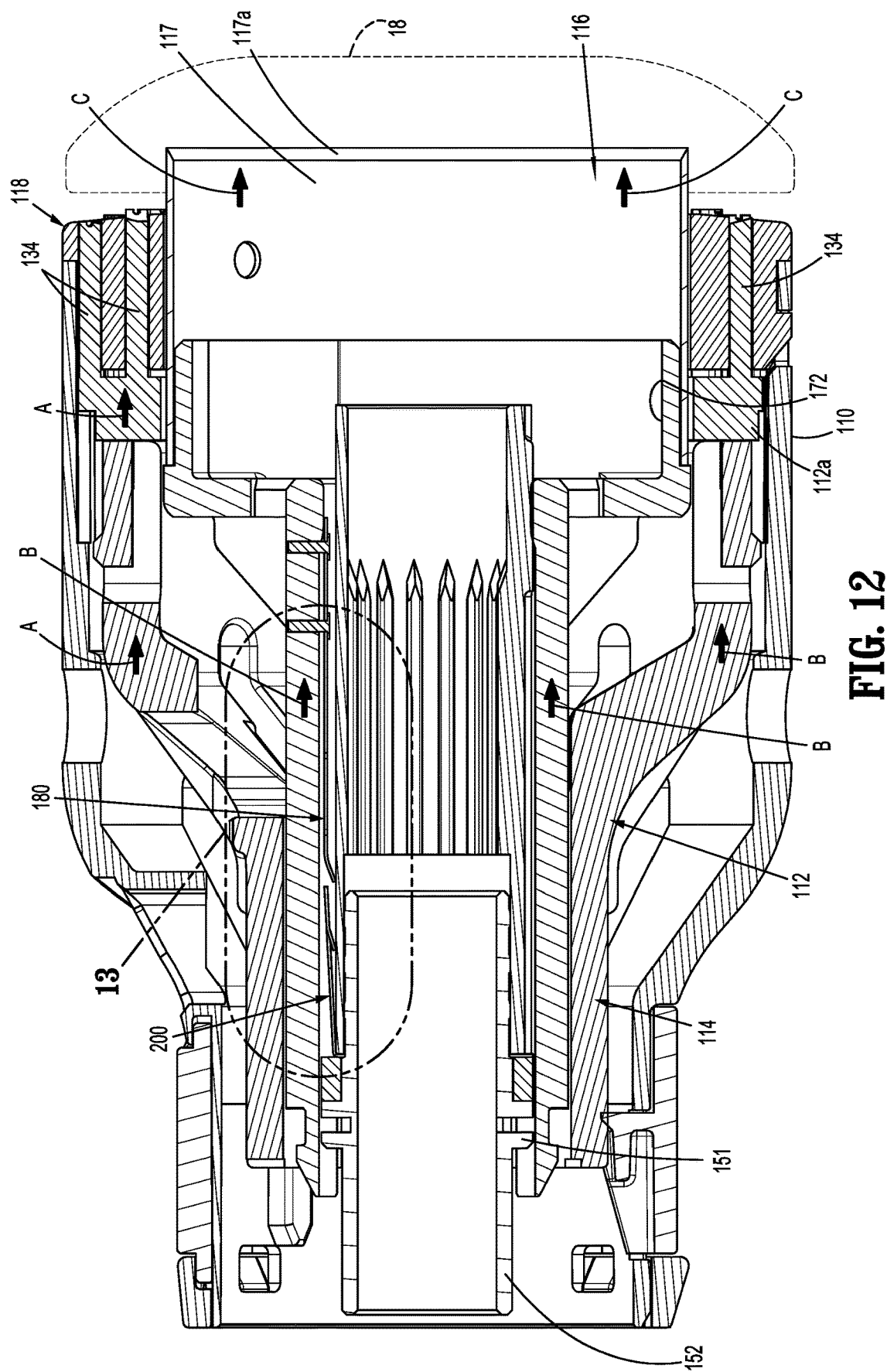
FIG. 12 is a cross-sectional view of the reload assembly shown in FIG. 3 taken through the longitudinal axis of the reload assembly with the reload assembly in a fired condition and the knife carrier in an advanced position.
Figure 13:
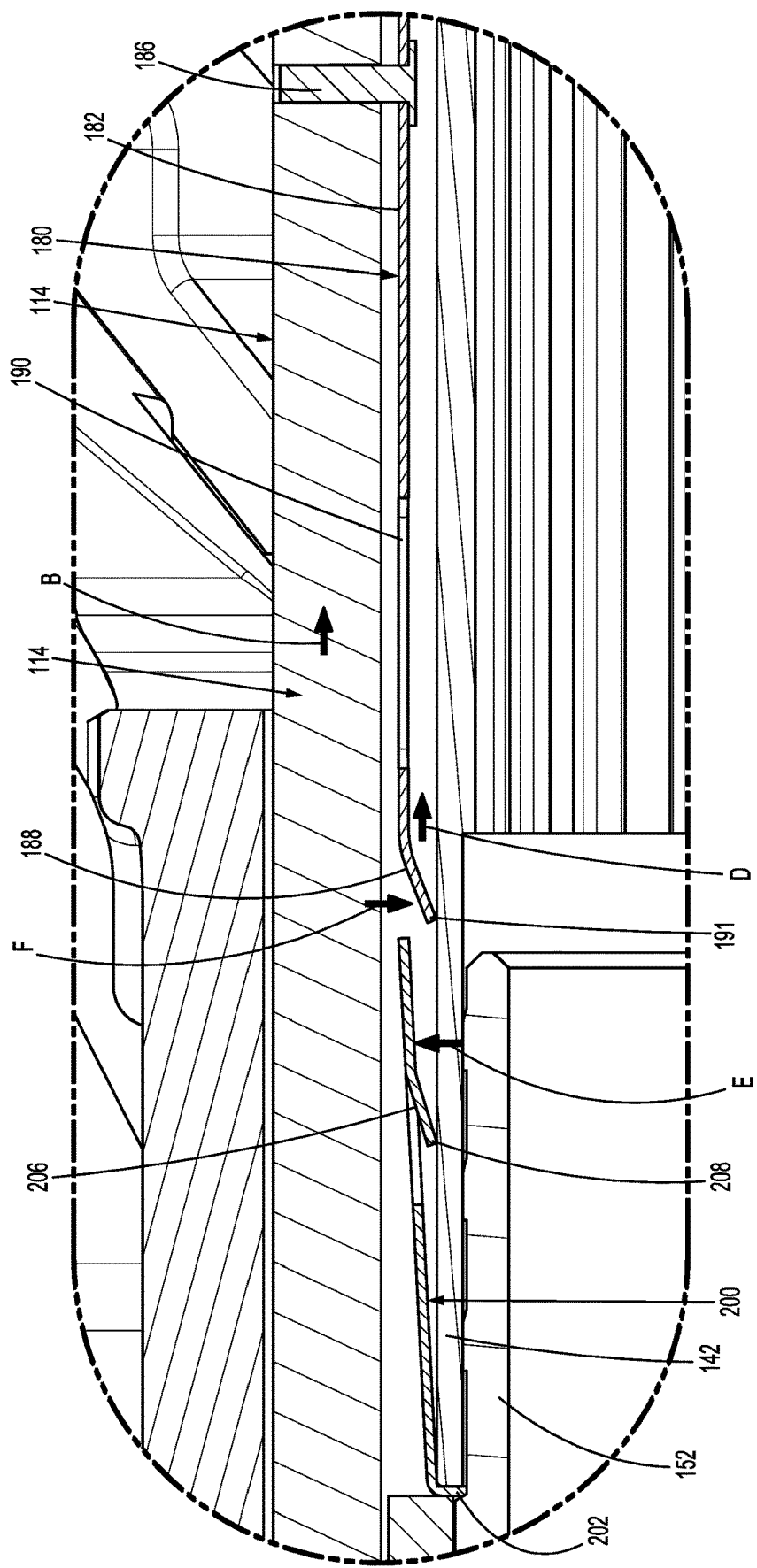
FIG. 13 is an enlarged view of the indicated area of detail shown in FIG. 12.

Referring to FIGS. 12 and 13, after the staple actuator 112 and the staple pushing member 112a are advanced in the direction indicated by arrows "A" to drive the staples 120 from the staple cartridge 118 into the anvil assembly 18, the knife carrier 114 is advanced in the direction indicated by arrow "B" to advance the knife 116 in the direction indicted by arrows "C" to cut tissue. When the knife carrier 114 advances in direction "B", the lockout component 180 which is secured to the knife carrier 114 moves longitudinally in relation to the hook component 200 in the direction indicated by arrow "D" (FIG. 13). When the lockout member 188 of the lockout component 180 moves to a position distally of the hook component 200, the hook 206 of the hook component 200 returns to an unbiased state as the body 204 of the hook component 200 moves radially outwardly from the inner housing portion 142 of the shell housing 110 in the direction indicated by arrow "E" in FIG. 13. In addition, when the lockout member 188 of the lockout component 180 moves distally of the hook component 200, the resilient body 182 moves out of engagement with the hook component 200 and inwardly towards its unbiased state in the direction indicated by arrow "F" in FIG. 13 such that the lockout member 188 of the lockout component 180 is engaged with the inner housing portion 142 of the shell housing 110 and is positioned radially inward of the distal end of the body 204 of the hook component 200.

Figure 14:
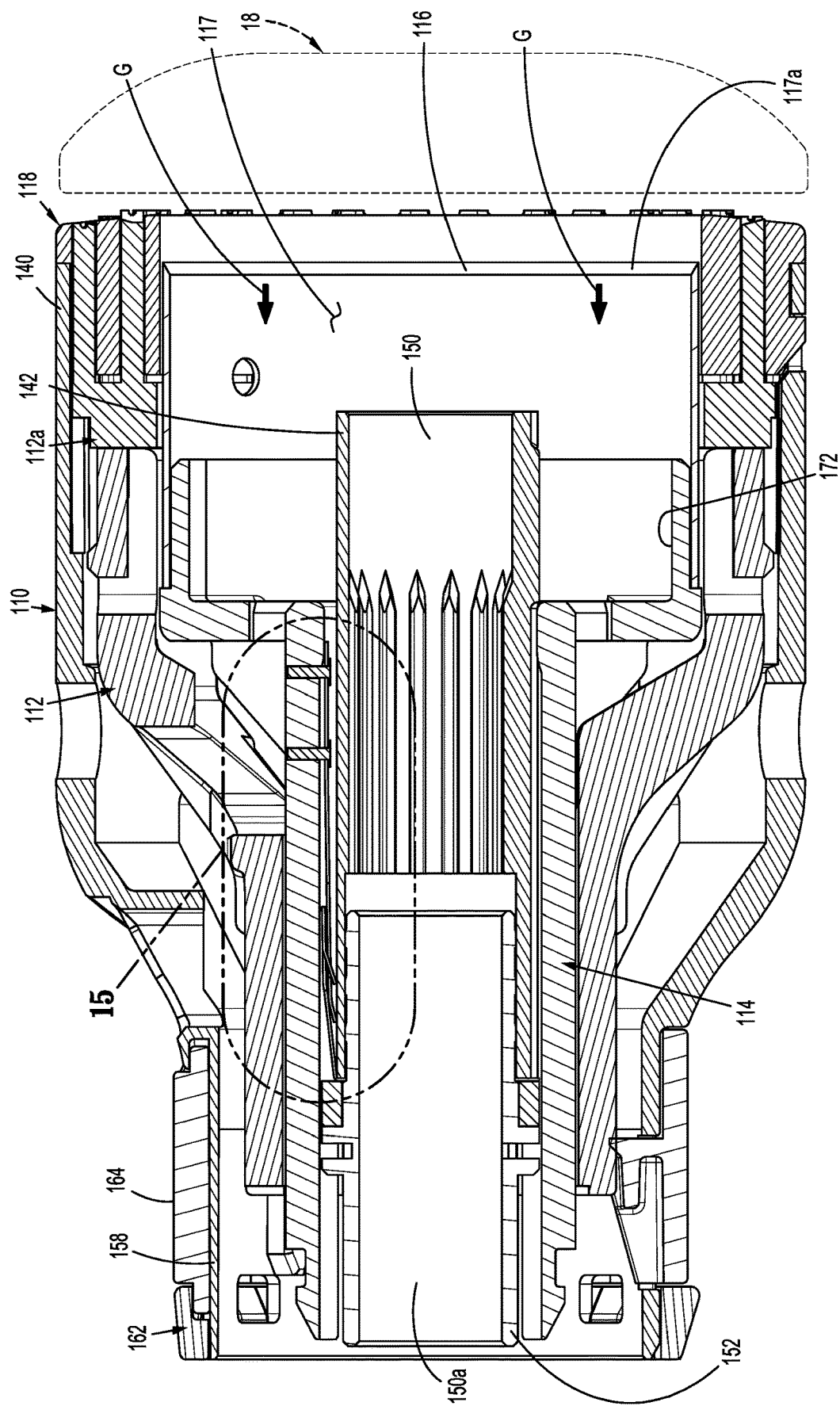
FIG. 14 is a cross-sectional view of the reload assembly shown in FIG. 3 taken through the longitudinal axis of the reload assembly with the reload assembly in a fired condition and the knife carrier in the retracted position.
Figure 15:
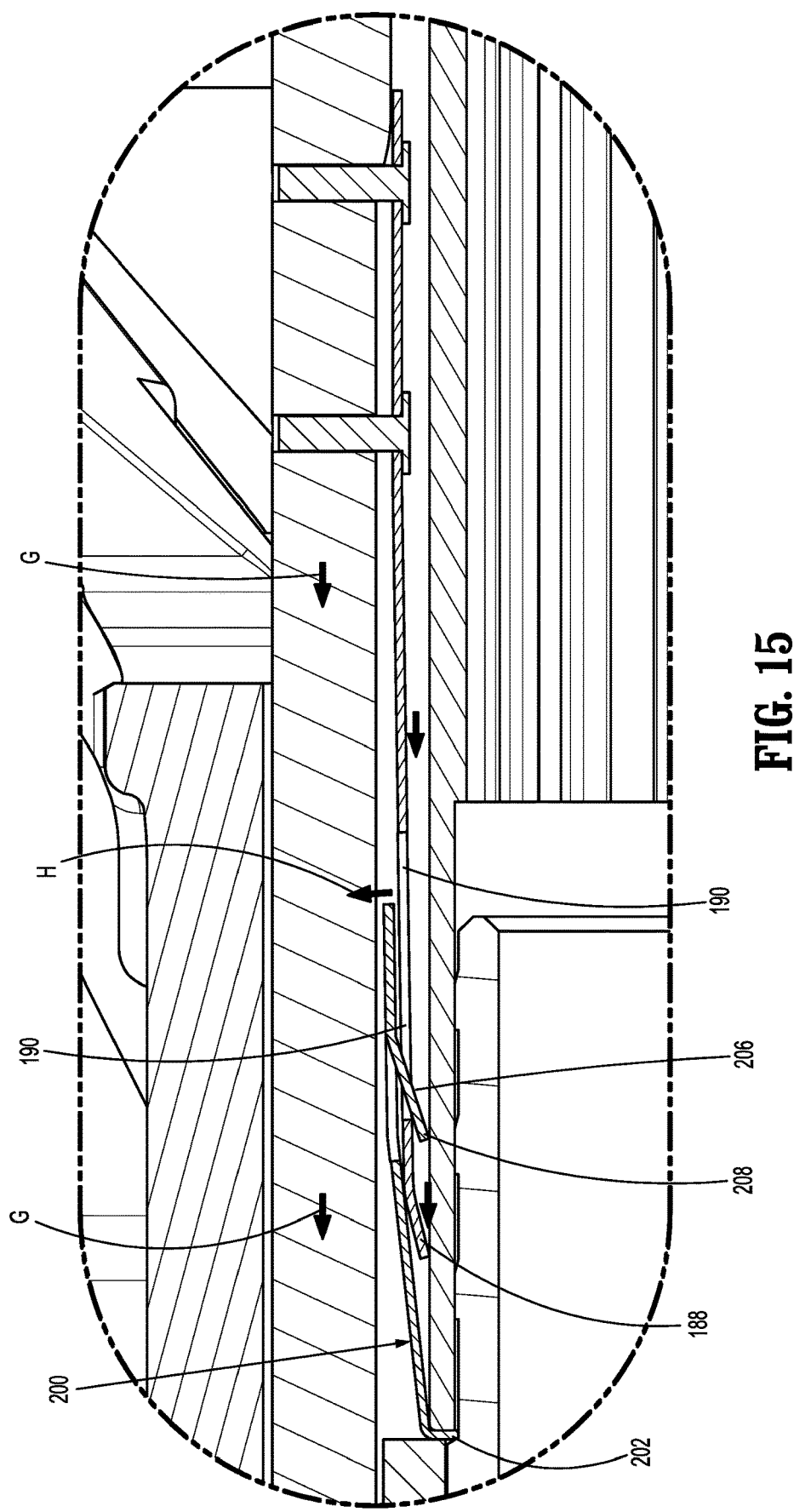
FIG. 15 is an enlarged view of the indicated area of detail shown in FIG. 14.
Figure 16:
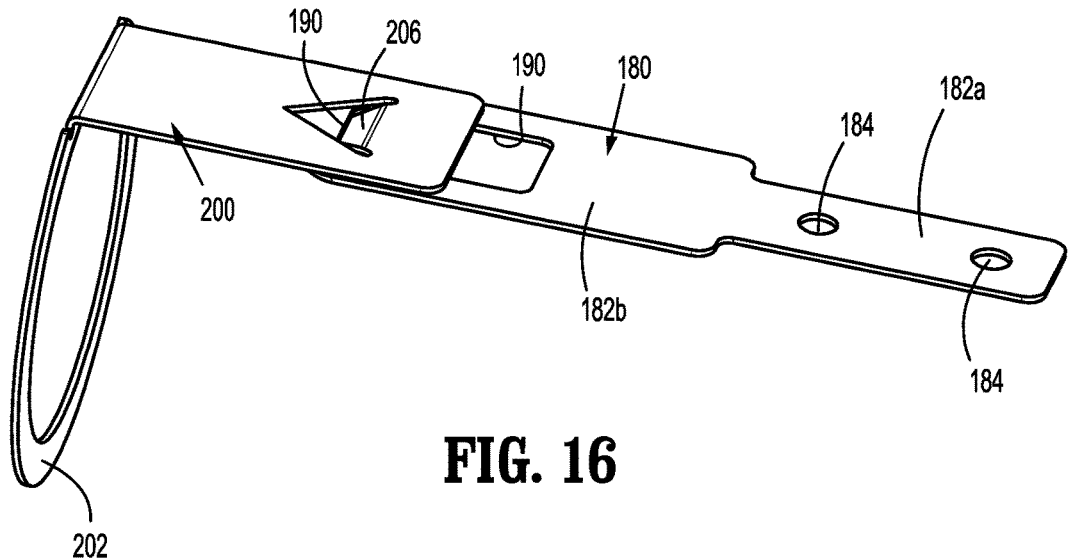
FIG. 16 is a side perspective view of the interaction between the locking component and the hook component of the reload assembly shown in FIG. 14 with the locking component and the hook component in a locked position.

Referring to FIGS. 14-17, when the knife carrier 114 is moved back to its retracted position after the reload assembly 100 is fired in the direction indicated by arrow "G" in FIGS. 14 and 15, the lockout member 188 of the lockout component moves under the body 204 of the hook component 200 and engages the hook 206 of the hook component 200. When the lockout member 188 engages the hook 206, the body 204 of the hook component 200 is biased radially outward of the inner housing portion 142 in the direction indicated by arrow "H" such that the lockout member 188 passes under the hook 206 and the hook 206 moves through the window 190 of the lockout component 180 such that the tip 191 of the lockout member 188 moves into engagement with the inner housing portion 142 of the shell housing 110. In this position, engagement between the hook 206 and the proximal portion of the body 182 of the lockout component 180 that defines the window 190 obstructs readvancement of the hook component 200 to obstruct readvancement of the knife carrier 114 and knife 116.

The above-described structure obstructs readvancement of the knife carrier 114 and the knife 116 to safely retain the knife 116 within the shell housing 110 of the reload assembly 100. This minimizes a risk of injury to a clinician during manipulation and disposal of the reload assembly 200.

Although the disclosed reload is described in the context of a powered hand instrument, it is to be understood that the disclosed reload can be adapted for use with robotically controlled systems as well as hand powered instruments. For example, the reload can be used with an adaptor 14 that is configured to be coupled to a robotically controlled surgical system.

Figure 17:
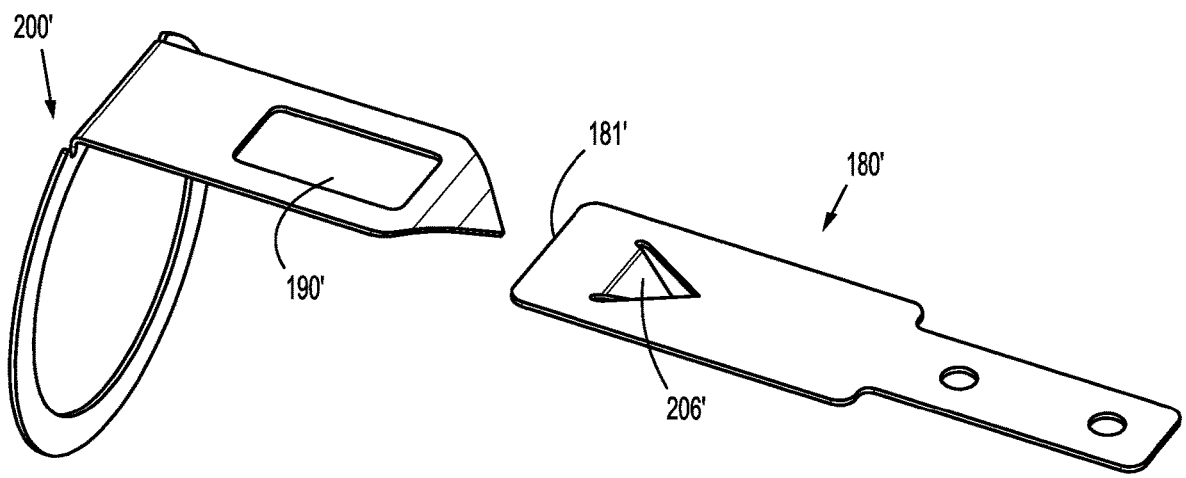
FIG. 17 is a side perspective view of another exemplary embodiment of the disclosed locking component and hook component of the reload assembly shown in FIG. 3.

Referring to FIG. 17, in an alternate embodiment, the lockout component 200' may be formed with a hook 206' and the hook component 200' may be formed with a body 204' defining a window 190'. The distal end of the lockout component 180' is positioned to pass over the lockout member 188' of the component 200' and onto the body 204 of the component 200' after the stapling device 10 (FIG. 1)

is fired and the knife carrier 114 (FIG. 12) is retracted such that the hook 206' is received within the window 190'. As discussed above with regard to the reload 100 (FIG. 3), receipt of the hook 206' within the window 190' obstructs readvancement of the knife carrier 114 (FIG. 12) to minimize risk of injury to a clinician during manipulation and disposal of the reload assembly 200.

FIGS. 18-22 illustrate an alternate embodiment of the disclosed reload assembly shown generally as 300. Reload assembly 300 is substantially similar to reload assembly 100 except that the lockout component and the hook component are modified. Only these components are described in further detail herein.

Figure 18:
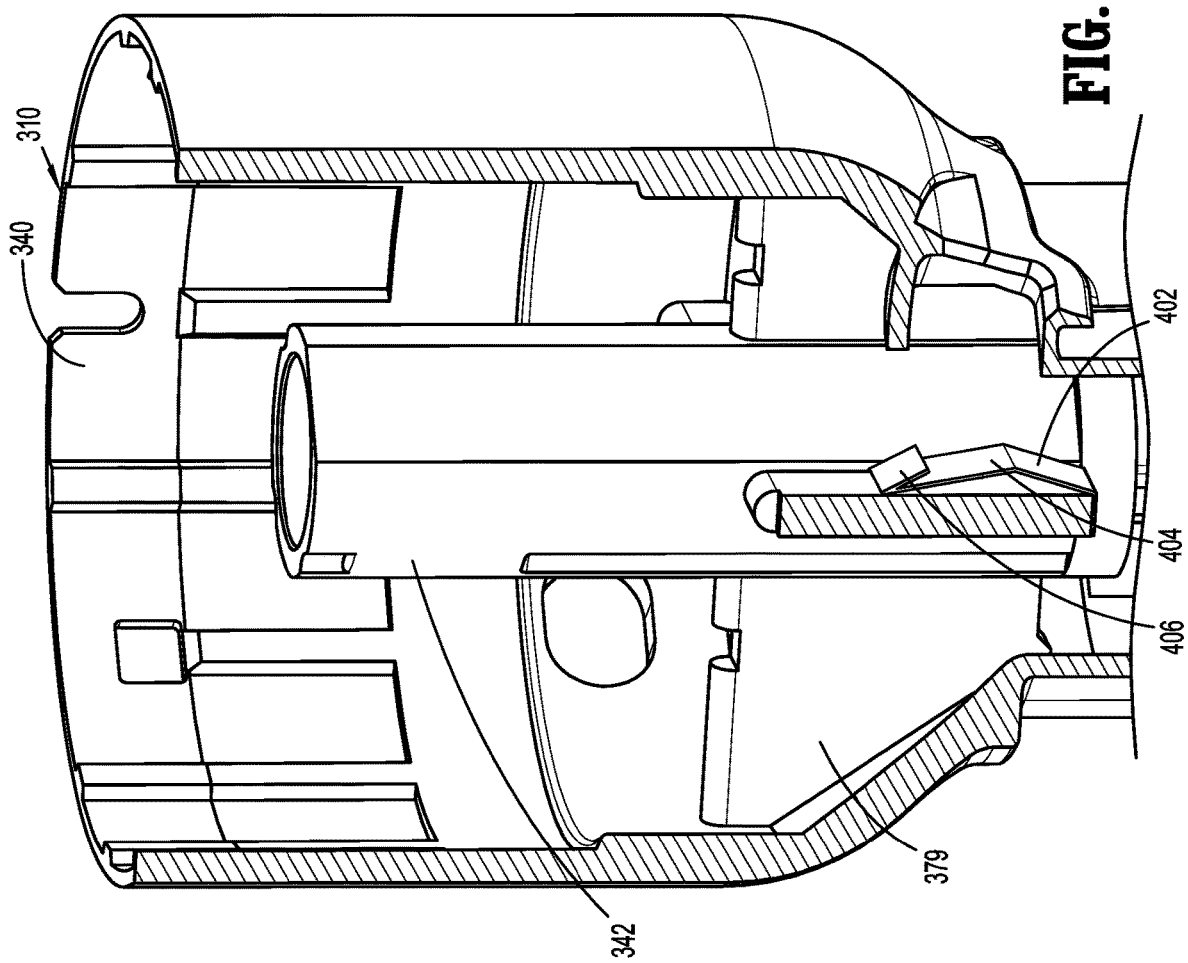
FIG. 18 is a perspective, cross-sectional view of a shell housing of another exemplary embodiment of the disclosed reload assembly of the stapling device shown in FIG. 1 with a locking component secured to an inner housing portion of the shell housing.

FIG. 18 illustrates a shell housing 310 of the reload assembly 300 (FIG. 20) which includes an outer housing portion 340, an inner housing portion 342, and guide portions 379. The guide portions 379 are positioned between the outer housing portion 340 and the inner housing portion 342. At least one of the guide portions 379 supports a first locking component 402. The first locking component 402 includes resilient body 404 having a hook 406 that extends radially outward from the respective guide portion 379.

Figure 19:
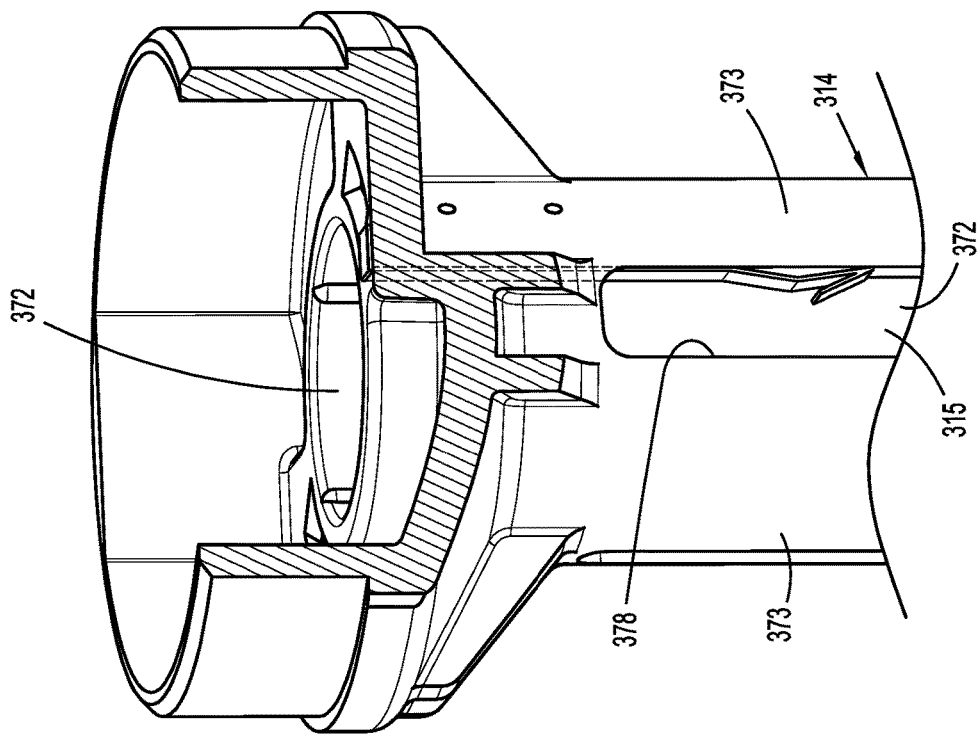
FIG. 19 is a perspective, cross-sectional view of the knife carrier of another exemplary embodiment of the disclosed reload assembly with a lock component secured to a body of the knife carrier.

FIGS. 18 and 19 illustrate the shell housing 310 and the knife carrier 314 of the reload assembly 300. The knife carrier 314 includes longitudinally extending body portions 373 that define a central bore 372. The longitudinally extending body portions 373 are separated from each other by longitudinal slots 378 that receive the guide portions 379 (FIG. 18) of the shell housing 310 to limit the knife carrier 314 to longitudinal movement within the shell housing 310 as the knife carrier 314 moves between advanced and retracted positions.

The proximal portion of knife carrier 314 includes an inner wall surface 315 that supports a second locking component 380 (FIG. 19). The second locking component 380 is formed from a resilient material and includes a proximal end having a second hook 382 that extends radially inward into the central bore 372 of the knife carrier 314. In embodiments, the first and second locking components 402 and 380, respectively, are formed from leaf springs.

Figure 20:
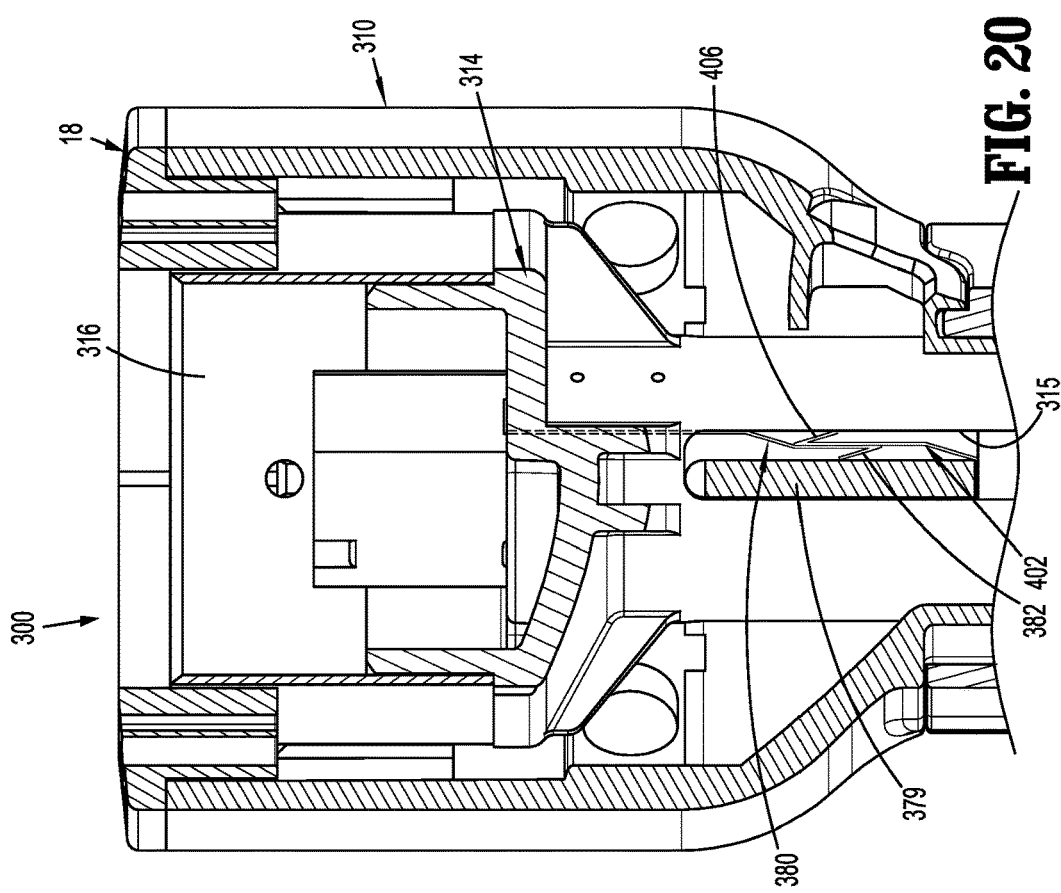
FIG. 20 is a cross-sectional view of a reload assembly including the locking component and hook component shown in FIGS. 18 and 19, respectively, with the reload assembly in a pre-fired condition.
Figure 22:
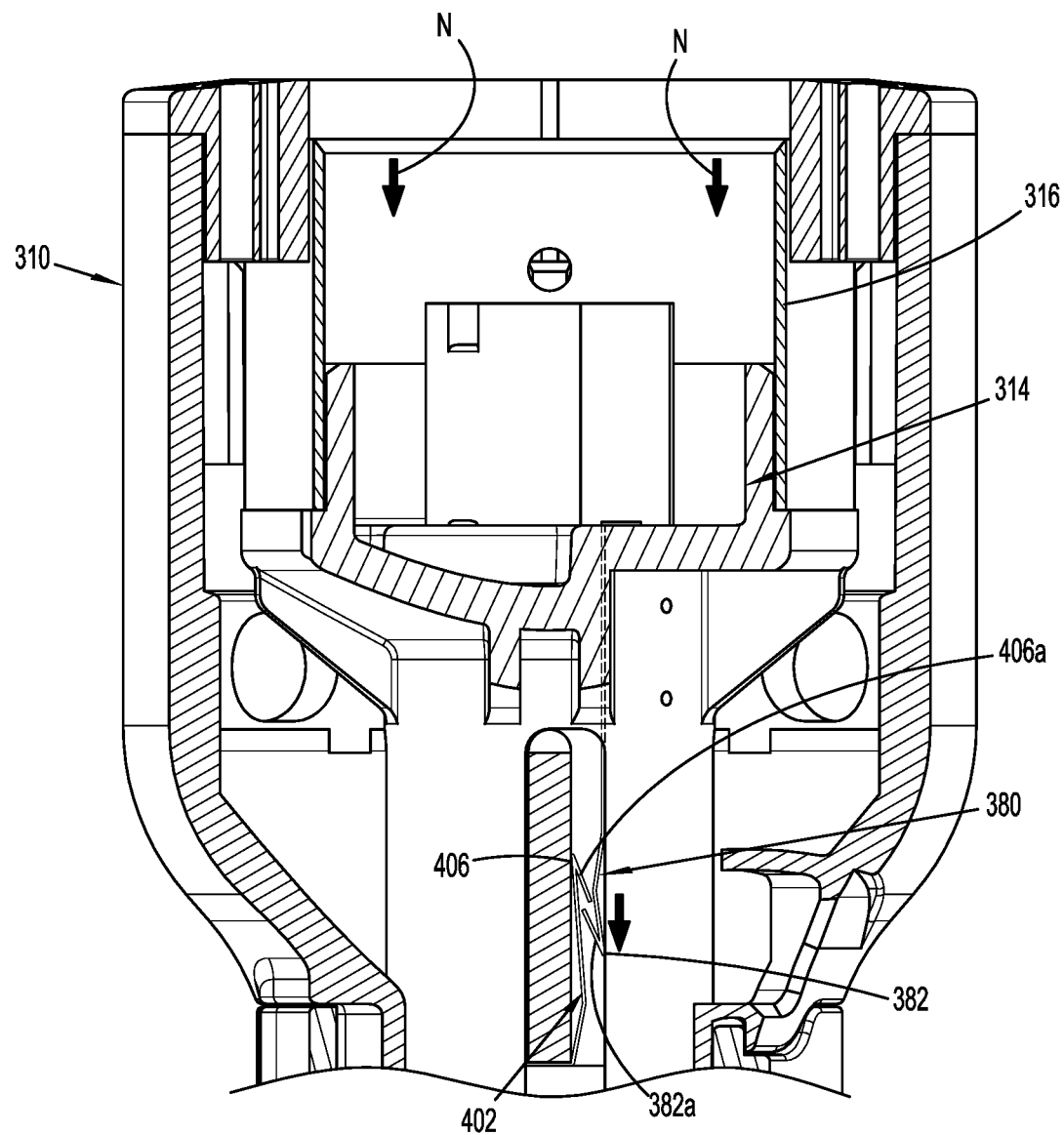
FIG. 22 is a cross-sectional view of the reload assembly shown in FIG. 20 with the reload assembly in a fired condition and the knife carrier in a retracted position.

When the reload assembly 300 is in a pre-fired position and the knife carrier 314 is in its retracted position as shown in FIG. 20, a side of the first locking component 402 opposite to the hook 406 is engaged with a side of the second locking component 380 opposite the hook 382. In this position, the first locking component 402 is aligned and engaged with the second locking component 380 with the hooks 406 and 382 of the first and second locking components 402 and 380 facing away from each other to allow advancement of the knife carrier 314 and knife 316 in relation to the inner housing portion 342 of the shell housing 310.

Figure 21:
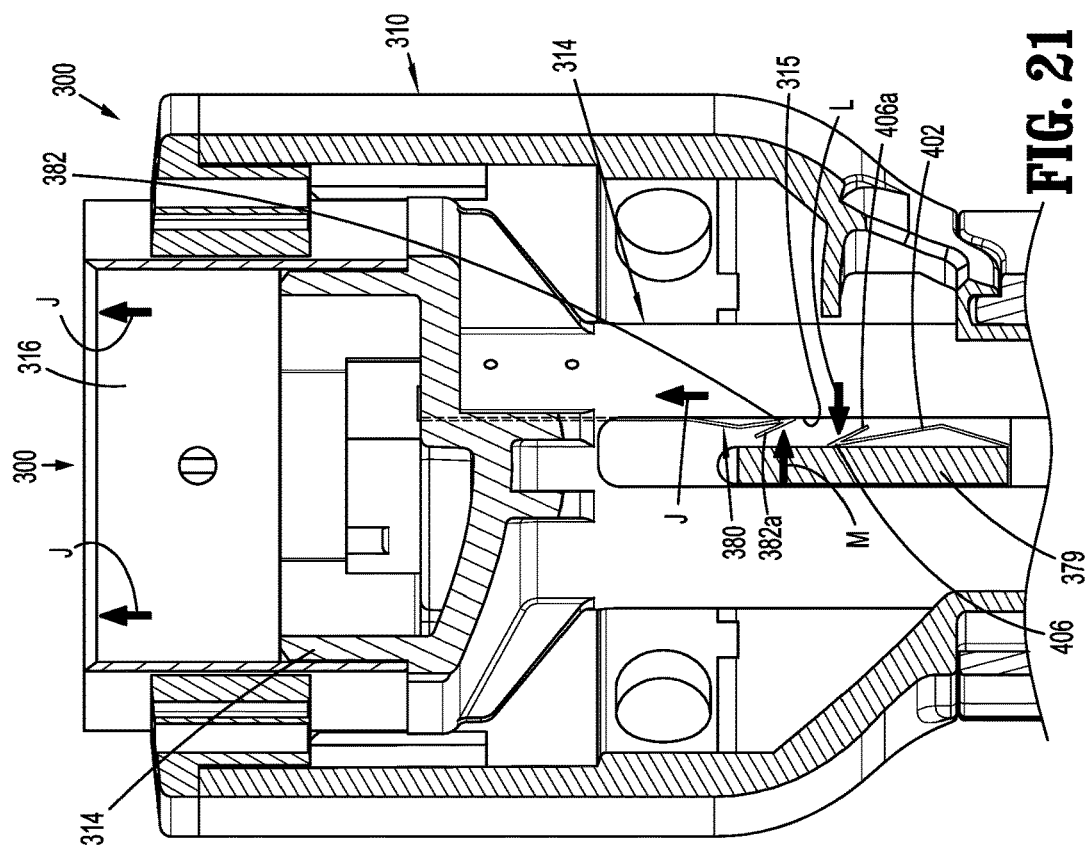
FIG. 21 is a cross-sectional view of the reload assembly shown in FIG. 20 with the reload assembly in a fired condition and the knife carrier in an advanced position.

When the knife carrier 314 is advanced in the direction indicated by arrows "J" in FIG. 21 about the inner housing portion 342 of the shell housing 310 to advance the second locking component 380 to a position distally of the first locking component 402, the first and second locking components 402 and 380 move out of engagement with each other. When this occurs, the first locking component 402 returns in the direction indicated by arrow "L" to its unbiased state in which the side of the first locking component 402 opposite to the first hook 406 is positioned against the guide 379. Similarly, the second locking component 380 returns in the direction indicated by arrow "M" to its unbiased state in which the side of the second locking component 380 opposite to the hook 382 is positioned against the inner wall surface 315 of the knife carrier 314.

When the first and second locking components 402 and 380 return to their unbiased states, tapered surfaces 406a and 382a of the hooks 406 and 382 are spaced and aligned with each other.

When the knife carrier 314 is moved from its advanced position back to its retracted position in the direction indicated by arrows "N" (FIG. 22) after the stapling device 10 (FIG. 1) has been fired and the knife has been advanced to cut tissue disposed between the anvil assembly 18 and the staple cartridge 118, the second locking component 380 moves in relation to the first locking component 402 such that the tapered surfaces 406a and 382a of the hooks 406 and 382 engage each other, deform, and pass by each other. When the knife carrier 114 is in its retracted position, the hooks 406 and 380 are aligned with each other to obstruct movement of the knife carrier 314 and knife 316 back to their advanced positions.

The above-described structure obstructs readvancement of the knife carrier 314 and the knife 316 to safely retain the knife 316 within the shell housing 310 of the reload assembly 300. This minimizes a risk of injury to a clinician during manipulation and disposal of the reload assembly 300.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:
1. A reload assembly comprising:
 a shell housing including an inner housing portion and an outer housing portion, the inner housing portion spaced from the outer housing portion to define an annular cavity between the inner and outer housing portions;
 a staple cartridge supported on a distal portion of the shell housing, the staple cartridge having a plurality of staple pockets, each of the staple pockets receiving a staple;
 a pusher supported within the annular cavity, the pusher movable between a retracted position and an advanced position to eject the staples from the staple cartridge;
 a knife carrier including a body defining a longitudinal axis and supporting a knife, the body of the knife carrier including an inner wall defining a central bore, the inner housing portion of the shell housing being positioned within the central bore of the knife carrier such that the knife carrier is movable about the inner housing portion of the shell housing between advanced and retracted positions;
 a lockout component supported on the inner wall of the knife carrier, the lockout component having a body formed of a resilient material and defining a window; and
 a hook component supported on the inner housing portion of the shell housing and including a body having a hook that is received within the window of the lockout component when the knife carrier is in its retracted position after the reload assembly is fired to obstruct movement of the knife carrier back to its advanced position.

2. The reload assembly of claim 1, wherein the lockout component includes a resilient body having a lockout member positioned proximally of the window, the resilient body being positioned between the hook component and the knife carrier when the knife carrier is in a retracted position prior to firing of the reload assembly.

3. The reload assembly of claim 2, wherein the hook is angled downwardly towards the inner housing portion of the shell housing.

4. The reload assembly of claim 3, wherein the hook component includes a proximal mounting portion that is secured to the inner housing portion such that the hook component is supported in cantilevered fashion to the inner housing portion of the shell housing.

5. The reload assembly of claim 4, wherein the lockout component is positioned to pass between the hook component and the inner housing portion of the shell housing when the knife carrier is returned from its advanced position to its retracted position after the reload assembly is fired to position the hook of the hook component within the window of the lockout component.

6. The reload assembly of claim 5, wherein the lockout component includes a distal mounting portion that is secured to the inner wall of the knife carrier to secure the lockout component to the knife carrier in cantilevered fashion.

7. The reload assembly of claim 6, wherein the hook of the hook component has a proximal portion connected to the body and a tip that engages the inner housing portion of the shell assembly, the tip being positioned proximally of the proximal portion of the hook.

8. A circular stapling device comprising:
an elongate body having a proximal portion and a distal portion; and
a reload assembly supported on the distal portion of the elongate body, the reload assembly including:
a shell housing including an inner housing portion and an outer housing portion, the inner housing portion spaced from the outer housing portion to define an annular cavity between the inner and outer housing portions;
a staple cartridge supported on a distal portion of the shell housing, the staple cartridge having a plurality of staple pockets, each of the staple pockets receiving a staple;
a pusher supported within the annular cavity, the pusher movable between a retracted position and an advanced position to eject the staples from the staple cartridge;
a knife carrier including a body defining a longitudinal axis and supporting a knife, the body of the knife carrier including an inner wall defining a central bore, the knife carrier movable about the inner housing portion of the shell housing between advanced and retracted positions;
a lockout component supported on the inner wall of the knife carrier, the lockout component having a body formed of a resilient material and defining a window; and
a hook component supported on the inner housing portion of the shell housing and including a body having a hook that is received within the window of the lockout component when the knife carrier is in its retracted position after the reload assembly is fired to obstruct movement of the knife carrier back to its advanced position.

9. The circular stapling device of claim 8, wherein the lockout component includes a resilient body having a lockout member positioned proximally of the window, the resilient body being positioned between the hook component and the knife carrier when the knife carrier is in a retracted position prior to firing of the reload assembly.

10. The circular stapling device of claim 9, wherein the hook is angled downwardly towards the inner housing portion of the shell housing.

11. The circular stapling device of claim 10, wherein the hook component includes a proximal mounting portion that is secured to the inner housing portion such that the hook component is supported in cantilevered fashion to the inner housing portion of the shell housing.

12. The circular stapling device of claim 11, wherein the lockout component is positioned to pass between the hook component and the inner housing portion of the shell housing when the knife carrier is returned from its advanced position to its retracted position after the reload assembly is fired to position the hook of the hook component within the window of the lockout component.

13. The circular stapling device of claim 12, wherein the lockout component includes a distal mounting portion that is secured to the inner wall of the knife carrier to secure the lockout component to the knife carrier in cantilevered fashion.

14. The circular stapling device of claim 13, wherein the hook of the hook component has a proximal portion connected to the body and a tip that engages the inner housing portion of the shell assembly, the tip being positioned proximally of the proximal portion of the hook.

* * * * *